United States Patent [19]

Viegas et al.

[11] Patent Number: 5,298,260
[45] Date of Patent: Mar. 29, 1994

[54] TOPICAL DRUG DELIVERY WITH POLYOXYALKYLENE POLYMER THERMOREVERSIBLE GELS ADJUSTABLE FOR PH AND OSMOLALITY

[75] Inventors: Tacey X. Viegas, Canton; Lorraine E. Reeve, Dexter, both of Mich.; Robert S. Levinson, Chesterfield, Mo.

[73] Assignee: Mediventures, Inc., Dearborn, Mich.

[21] Appl. No.: 895,949

[22] Filed: Jun. 9, 1992

Related U.S. Application Data

[63] Continuation-in-part of Ser. No. 517,282, May 1, 1990, abandoned.

[51] Int. Cl.[5] .......................... A61K 9/10; A61K 47/34
[52] U.S. Cl. .................................. 424/486; 514/944; 523/105; 523/122; 252/315.1
[58] Field of Search .......................... 424/486; 514/944; 523/105, 122; 252/315.1

[56] References Cited

U.S. PATENT DOCUMENTS

| | | | |
|---|---|---|---|
| 2,674,619 | 4/1954 | Lundsted | 260/480 |
| 2,677,700 | 5/1954 | Jackson | 260/488 |
| 2,979,528 | 4/1961 | Lundsted | 260/584 |
| 3,036,118 | 5/1962 | Jackson | 260/484 |
| 3,535,307 | 10/1970 | Moss | 260/209 |
| 3,639,575 | 2/1972 | Schmolka | 424/78 |
| 3,740,421 | 6/1973 | Schmolka | 424/65 |
| 3,829,506 | 8/1974 | Schmolka | 260/615 B |
| 3,867,533 | 2/1975 | Schmolka | 424/258 |
| 4,439,196 | 3/1984 | Higuchi | 604/890 |
| 4,465,663 | 8/1984 | Schmolka | 424/62 |
| 4,474,752 | 10/1984 | Haslam et al. | 424/78 |
| 4,474,753 | 10/1984 | Haslam et al. | 424/78 |
| 4,511,563 | 4/1985 | Schmolka | 514/162 |
| 4,767,619 | 8/1988 | Murray | 424/78 |
| 4,810,503 | 3/1989 | Carson | 424/76.3 |
| 4,861,760 | 8/1989 | Mazuel | 514/54 |
| 4,883,660 | 11/1989 | Blackman | 424/78 |
| 5,071,644 | 12/1991 | Viegas | 515/772 |
| 5,077,033 | 12/1991 | Viegas | 514/668 |
| 5,124,151 | 6/1992 | Viegas | 424/422 |
| 5,126,141 | 6/1992 | Henry | 424/423 |
| 5,143,731 | 9/1992 | Viegas | 424/486 |

OTHER PUBLICATIONS

Schmolka, I. R., "Artificial Skin I Preparation and Properties of PLURONIC® F-127 Gels For Treatment of Burns", *Journal of Biomedical Material Research*, vol. 6 p. 571 (1972).

*Primary Examiner*—Edward Webman
*Attorney, Agent, or Firm*—Dykema Gossett

[57] ABSTRACT

Iso-osmotic, hyperosmotic, or hypo-osmotic, pH balanced, thermoreversible gels are ideal medical devices or vehicles for drug delivery to the skin of a mammal. The osmolality in the gel state can be calculated by assuming that a polyoxyalkylene block copolymer or polyether present in said gel does not contribute to the osmolality in the gel state, although it does contribute to the measured osmolality in the liquid state.

23 Claims, 1 Drawing Sheet

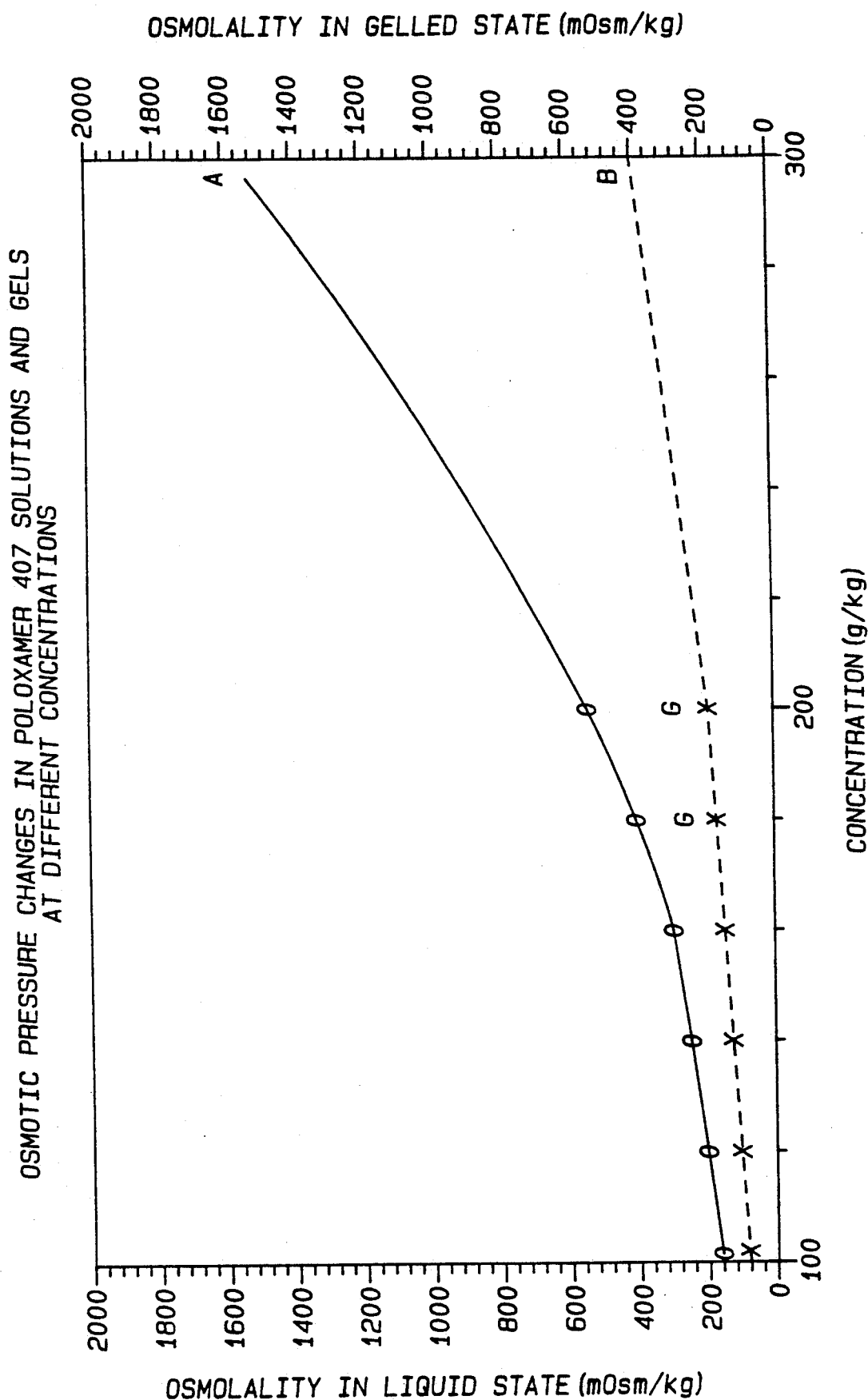

TOPICAL DRUG DELIVERY WITH POLYOXYALKYLENE POLYMER THERMOREVERSIBLE GELS ADJUSTABLE FOR PH AND OSMOLALITY

This is a continuation-in-part of copending application Ser. No. 07/517,282 filed on May 1, 1990, now abandoned.

BACKGROUND OF THE INVENTION

1. Field of the Invention

This invention relates to drug delivery systems comprising an aqueous gel.

2. Description of the Prior Art

Over the years, methods have been developed to achieve the efficient delivery of a therapeutic drug to a mammalian body part requiring pharmaceutical treatment. Use of an aqueous liquid which can be applied at room temperature as a liquid, but which forms a semisolid gel when warmed to body temperature, has been utilized as a vehicle for drug delivery since such a system combines ease of application with greater retention at the site requiring treatment than would be the case if the aqueous composition were not converted to a gel as it is warmed to mammalian body temperature. In U.S. Pat. No. 4,188,373, PLURONIC® polyols are used in aqueous compositions to provide thermally gelling aqueous systems. Adjusting the concentration of the polymer provides the desired sol-gel transition temperature, that is, the lower the concentration of polymer, the higher the sol-gel transition temperature, after crossing a critical concentration minimum below which a gel will not form.

In U.S. Pat. Nos. 4,474,751; '752; '753; and 4,478,822 drug delivery systems are described which utilize thermosetting gels; the unique feature of these systems is that both the gel transition temperature and/or the rigidity of the gel can be modified by adjustment of the pH and/or the ionic strength, as well as by the concentration of the polymer.

Other patents disclosing pharmaceutical compositions which rely upon an aqueous gel composition as a vehicle for the application of the drug are U.S. Pat. Nos. 4,883,660; 4,767,619; 4,511,563; and 4,861,760. Thermosetting gel systems are also disclosed for application to injured mammalian tissues of the thoracic or peritoneal cavities in U.S. Pat. No. 4,911,926.

While the prior art is silent with respect to aqueous drug delivery vehicles and isotonicity thereof, osmotic drug delivery systems are disclosed in U.S. Pat. No. 4,439,196 which utilize a multi-chamber compartment for holding osmotic agents, adjuvants, enzymes, drugs, pro-drugs, pesticides, and the like. These materials are enclosed by semipermeable membranes so as to allow the fluids within the chambers to diffuse into the environment into which the osmotic drug delivery system is in contact. The drug delivery device can be sized for oral ingestion, implantation, rectal, vaginal, or occular insertion for delivery of a drug or other beneficial substance. Since this drug delivery device relies on the permeability of the semipermeable membranes to control the rate of delivery of the drug, the drugs or other pharmaceutical preparation, by definition, are not isotonic with mammalian blood.

SUMMARY OF THE INVENTION

Drug delivery vehicles, drug delivery compositions, and medical devices and processes for their use are disclosed. The pharmaceutical compositions containing pharmacologically active medicaments are useful in providing treatments to various parts of the mammalian body requiring pharmacological treatment. The pharmaceutical compositions in one embodiment of the invention provide a physiologically acceptable media having a buffered pH and an osmotically balanced vehicle so as to, preferably, provide an isotonic mixture which is iso-osmotic with body fluids and has a similar pH to body fluids, such as blood plasma and the extracellular fluid of exposed tissue, such as found in the area of third degree burn tissue. The pH and iso-osmotic pressure of such bodily fluids is about pH 7.4 and 290 mOsm/kg. The use of the compositions of the invention as a medical device and without a drug component is indicated where an aqueous gel is desirable to separate injured tissue in a manner more gentle than can be accomplished using surgical instruments. In addition, the pharmaceutical compositions are, optionally, sterilized so as to insure that the pharmaceutical compositions of the invention do not provide a source of infection.

Polyphase systems are also useful and may contain non-aqueous solutes, non-aqueous solvents, and other non-aqueous additives. Homogeneous, polyphase systems can contain such additives as water insoluble high molecular weight fatty acids and alcohols, fixed oils, volatile oils and waxes, mono-, di-, and triglycerides, and synthetic, water insoluble polymers without altering the functionality of the system.

In a preferred embodiment, the compositions of the invention can be delivered to the area of the mammalian body requiring treatment as a low viscosity liquid at ambient temperatures which, upon contact with the mammalian body, forms a semisold gel having a very high viscosity. Because the preferred pharmaceutical compositions of the invention are low viscosity liquids at ambient temperatures, they easily pass around hair and reach the underlying skin insuring maximum contact between exposed tissue and the pharmaceutical composition of the invention. If necessary, the preferred pharmaceutical compositions of the invention can be washed away under a gentle stream of cool water, thus minimizing the risk of further injury and pain to the patient upon removal.

A wide variety of polyoxyalkylene polymers are suitable for the preparation of the pharmaceutical compositions of the invention. Generally, it is necessary to adjust for a minimum polymer concentration in aqueous solution so as to obtain the desired sol-gel transition temperature in order that the compositions can be provided as low viscosity liquids at ambient temperature, yet form stiff semisold gels at mammalian body temperatures. In addition to the concentration of the polymer and the concentration of the water soluble or dispersible pharmacologically active medicaments, other suitable excipients must be added so as to provide the desired isotonic and iso-osmotic properties.

The useful polymers which provide the sol-gel characteristics of the pharmaceutical compositions of the invention are, preferably, polyoxyalkylene block copolymers.

DESCRIPTION OF THE DRAWING

The drawing, FIG. 1, provides a curve showing the osmolality in the solution state of a polyoxyalkylene block copolymer, identified as Poloxamer 407, at various concentrations in a 0.1 molar TRIS hydrochloride buffer. The scale at the left side of the plot indicates the osmolality in the liquid state, while the scale on the right side of the plot indicates the osmolality of the composition when in the gelled state. Thus, curve A provides a graph showing the osmolality in the liquid state at various concentrations in grams per kilogram of the Poloxamer 407. Curve B shows the osmolality calculated for the gel state assuming that the molecules of Poloxamer 407 when gelled will not contribute to osmotic force. Curve A is obtained by measuring the effect solutions in comparison with a sample of purified water (deionized water). It is noted that the curves were obtained by fitting the osmolality and concentration of polymer to the quadratic equation, $Y = A + Bx + Cx^2$, where Y is osmolality, x is concentration, and A, B, and C are constants. The relationship of concentration to osmolality is nonlinear in this system.

DETAILED DESCRIPTION OF THE INVENTION

It has been found that aqueous pharmaceutical vehicles containing a polyoxyalkylene block copolymer, which have the unique feature, in a preferred embodiment, of being liquid at ambient temperatures and transitioning at mammalian body temperatures to a semisold gel, can be made isotonic or iso-osmotic (or hyperosmotic or hypo-osmotic) and adjusted to the pH of mammalian body fluids, such as blood plasma and extracellular fluid, as results in the area of third degree burns. The pH and osmotic pressure of such bodily fluids are 7.5 and 290 mOsm/kg, respectively. It is, advantageous to deliver a pharmacologically active medicament to an area of the mammalian body requiring pharmacological treatment under pH and osmotic pressure conditions which match those of bodily fluids. Optionally, the medical devices and the pharmaceutical compositions of the invention can be provided in a sterile condition.

In addition to those polyoxyalkylene polymers described above, which are suitable in the formation of the pharmaceutical compositions of the invention, other polyoxyalkylene polymers which form gels at low concentrations in water are suitable. One such polymer is described in U.S. Pat. No. 4,810,503, incorporated herein by reference. These polymers are prepared by capping conventional polyether polyols with an alpha-olefin epoxide having an average of about 20 to about 45 carbon atoms, or mixtures thereof. Aqueous solutions of these polymers gel in combination with surfactants, which can be ionic or nonionic. The combination of the capped polyether polymers and the surfactants provide aqueous gels at low concentrations of the capped polymer and surfactant, which generally do not exceed 10% by weight total. Detailed methods of preparing these aqueous gels are disclosed in U.S. Pat. No. 4,810,503. Preparation of said aqueous gels is generally described below. Preferred surfactants for use in preparing these gels are also disclosed in said patent.

A conventional copolymer polyether polyol is prepared by preparing block or heteric intermediate polymers of ethylene oxide and at least one lower alkylene oxide having 3 to 4 carbon atoms as intermediates. These are then capped with the alpha-olefin epoxide to prepare the polymers. Ethylene oxide homopolymers capped with said alpha-olefin oxides are also useful as intermediates.

The heteric copolymer intermediate is prepared by mixing ethylene oxide and at least one lower alkylene oxide having 3 to 4 carbon atoms with a low molecular weight active hydrogen-containing compound initiator having at least two active hydrogens and preferably, 2 to 6 active hydrogen atoms such as a polyhydric alcohol, containing from 2 to 10 carbon atoms and from 2 to 6 hydroxyl groups, heating said mixture to a temperature in the range of about 50° C. to 150° C., preferably from 80° C. to 130° C., under an inert gas pressure preferably from about 30 psig to 90 psig.

A block copolymer intermediate is prepared by reacting either the ethylene oxide or said alkylene oxide having 3 to 4 carbon atoms with said active hydrogen-containing compound followed by reaction with the other alkylene oxide.

The ethylene oxide and the alkylene oxides having from 3 to 4 carbon atoms are used in said intermediates in amounts so that the resulting polyether product will contain at least 10 percent by weight, preferably about 70 percent to about 90 percent by weight, ethylene oxide residue. The ethylene oxide homopolymer intermediate is hydrogen-containing compound. The reaction conditions for preparing the block copolymer and ethylene oxide homopolymer intermediates are similar to those for the heteric copolymer intermediate. The temperature and pressure are maintained in the above ranges for a period of about one hour to ten hours, preferably one to three hours.

The alpha-olefin oxides which are utilized to modify the conventional polyether intermediate of the prior art are those oxides and the commercially available mixtures thereof generally containing an average of about 20 to 45, preferably about 20 to 30, carbon atoms. The amount of alpha-olefin required to obtain the more efficient capped polyethers is generally about 0.3 to 10 percent, preferably about 4 to 8 percent, of the total weight of the polyethers.

Since the preparation of heteric and block copolymers of alkylene oxides and ethylene oxide homopolymers are well known in the art, further description of the preparation of said polymers is unnecessary. Further details of the preparation of eteric copolymers of lower alkylene oxide can be obtained in U.S. Pat. No. 3,829,506, incorporated herein by reference. Further information on the preparation of block copolymers of lower alkylene oxides can be obtained in U.S. Pat. Nos. 3,535,307; 3,036,118; 2,979,578; 2,677,700; and 2,675,619 incorporated herein by reference.

The surfactants may be ionic or nonionic and many surfactants and types of surfactants may be employed. While all surfactants may not be effective in the preparation of the isotonic gels of the instant invention, the fact that many are effective makes it a simple matter for one skilled in the art to select such surfactant with a minimum of trial and error.

The amounts of capped polyether polymer and surfactant may be as little as 1.0 percent by weight or less of each depending on the type and amount of the other component. There appears to be no maximum amount of either component than that dictated by economic considerations. However, the total amount of capped polymer and surfactant would generally not exceed 10 percent by weight.

Generally, the polyoxyalkylene block copolymers of the invention are defined as follows:

a polyoxyalkylene block copolymer of the formula $$Y[(A)_n-E-H]_x \quad \text{(I)}$$

wherein A is a polyoxyalkylene moiety having an oxygen/carbon atom ratio of less than 0.5, x is at least 2, Y is derived from water or an organic compound containing x reactive hydrogen atoms, E is a polyoxyethylene moiety constituting at least 60% by weight of the copolymer, n has a value such that the minimum molecular weight is between about 500 and about 900, as determined by the hydroxyl number of an intermediate, $$Y[(A)_n-H]_x \quad \text{(II)}$$

and the total average molecular weight of the copolymer is at least about 5000.

Preferred are polyoxyalkylene block copolymers of the formula:

$$HO(C_2H_4O)_b(C_4H_8O)_a(C_2H_3O)_bH \quad \text{(III)}$$

wherein in III, a is an integer such that the hydrophobe base represented by $(C_4H_8O)_a$ has a molecular weight of at least about 500 as determined by hydroxyl number, the polyoxyethylene chain constituting at least about 70% by weight of the copolymer, and the copolymer having a total average molecular weight of at least 15,000 or $$HO(C_2H_4O)_b(C_3H_6O)_a(C_2H_4O)_bH \quad \text{(IV)}$$

wherein in IV, a is an integer such that the hydrophobe base represented by $(C_3H_6O)_a$ has a molecular weight of at least about 900 average molecular weight, as determined by hydroxyl number, the polyoxyethylene chain constitutes at least about 70% by weight of the copolymer, and the copolymer having a total average molecular weight of at least about 15,000 or

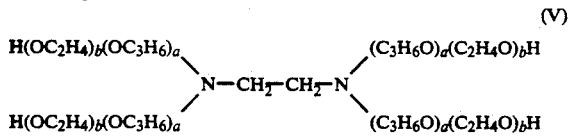

(V)

wherein in V, a and b are integers such that the copolymer has a hydrophobe molecular weight of at least about 1500, a hydrophile content of at least about 70%, and a total average molecular weight of at least about 15,000.

Most preferred are the polyoxyalkylene block copolymers of the formula:

$$H[OCH_2CH_2]_{49}[OCHCH_2]_{67}[OCH_2CH_2]_{49}OH \quad \text{(VI)}$$
$$\phantom{H[OCH_2CH_2]_{49}[O}|\phantom{HCH_2]_{67}[OCH_2CH_2]_{49}OH}$$
$$\phantom{H[OCH_2CH_2]_{49}[O}CH_3$$

These polymers are present, preferably, in the amount of about 10 to about 30% by weight of the total weight of the compositions of the invention.

In general, the preferred drug delivery vehicle of the present invention will contain a pharmacologically effective amount, preferably, from about 0.01% to about 60% by weight of the medicament or pharmaceutical, from about 10 to about 50% of the polymer and from 80% to about 20% water. In special situations, however, the amounts may be varied to increase or decrease the dosage schedule.

If desired, the drug delivery vehicle may also contain preservatives, co-solvents, suspending agents, viscosity enhancing agents, osmolality adjusters, coloring agents, and other excipients in addition to the medicament and buffering agents. Suitable water soluble preservatives which may be employed in the drug delivery vehicle are sodium bisulfite, sodium thiosulfate, ascorbate, benzalkonium chloride, chlorobutanol, thimerosal, phenylmercuric borate, parabens, benzyl alcohol and phenyl ethanol, and others. These agents may be present in amounts of about 0.001% to about 5% by weight and, preferably, in the amount of about 0.01 to about 2% by weight.

Suitable water soluble buffering agents are alkali or alkali earth carbonates, phosphates, bicarbonates, citrates, borates, acetates, succinates and the like, such as sodium phosphate, citrate, borate, acetate, bicarbonate and carbonate. Organic buffering agents such as trorethamine (TRIS) may also be used. These agents are present in amounts sufficient to maintain the pH of the system at 7.4±0.2 and preferably 7.4. As such the buffering agent can be as much as 5% by weight of the total composition.

With specific reference to the use of the pharmaceutical compositions of the invention for administration to the skin of a mammal, it is contemplated to use suitable medicaments such as antibacterial substances, anti-infectives, anesthetics, anti-inflammatories, antiparasitics, antivirals, antifungals, analgesics, and diagnostics. Representative antibacterial substances are the antibacterial substances selected from the group consisting of beta-lactam antibiotics, tetracyclines, chloramphenicol, neomycin, gramicidin, bacitracin, sulfonamides, animoglysoside antibiotics, tobramycin, nitrofurazone, nalidixic acid and analogs, the antimicrobial combination of fluoroalanine pentizidone, mafenide acetate, silver sulfadiazine, and nitrofurazone. Representative beta-lactam antibiotics or representative anti-infectives are iodine, chloramines, benzalkonium chloride and phenol. Representative anti-inflammatory drugs are cortisone, hydrocortisone, betamethasone, dexamethasone, fluocortolone, prednisolone, triamcinolone, indomethacin, sulindac and its salts and corresponding sulfide. A representative antiparasitic drug is ivermectin. Representative antiviral drugs are acyclovir and interferon. Representative anesthetic drugs are benzocaine, lidocaine and dibucaine. Representative antifungal drugs are tolnaftate, undecylenic acid, salicylic acid, zinc undecylenate miconazole, and thiabendazole. Representative analgesic drugs are methylsalicylate, menthol, camphor, methylnicotinate, triethanolamine salicylate, glycol salicylate and salicylamine. Representative diagnostic compounds are n-alkyl carbonates, cholesteryl oleyl carbonate, cholesteryl nonanoate or cholesteryl benzoate all in proper proportions to effect liquid crystal responses.

Representative buffering agents or salts useful in maintaining the pH at about 7.4±0.2 are tromethamine (TRIS) and alkali or alkali earth carbonates, chlorides, sulfates, phosphates, bicarbonates, citrates, borates, acetates and succinates. Representative preservatives are sodium bisulfite, sodium thiosulfate, ascorbate, benzalkonium chloride, chlorobutanol, thimerosal, phenylmercuric borate, parabens, benzyl alcohol phenyl ethanol.

The preparation of the pharmaceutical drug delivery compositions of the invention are described below. The Examples which follow were prepared according to the following preparation procedure. Since the polymer systems of this invention dissolve more quickly and easily at reduced temperatures, the preferred methods of solubilization are to add the required amount of polymer to the amount of water to be used. Generally after wetting the polymer by shaking, the mixture is capped and placed in a cold chamber or in a thermostatic container at about 0° C. to 10° C. in order to dissolve the polymer. The mixture can be stirred or shaken to bring about a more rapid solution of the polymer. The pharmacologically active medicaments and various additives such as buffers, salts, and preservatives can subsequently be added and dissolved. In some instances the pharmacologically active substance must be suspended since it is insoluble in water. The pH of 7.4±0.2 is obtained by the addition of appropriate buffering agents. Other excipients may be added to adjust osmolality or to provide other excipient attributes.

The following Examples illustrate the various aspects of the invention but are not intended to limit its scope. Where not otherwise specified throughout this specification and claims, temperatures are given in degrees centigrade and parts, percentages, and proportions are by weight.

EXAMPLE 1

The Example formulation describes a composition characterized as iso-osmotic, sterile, and having a pH of 7.4±0.2. An aqueous solution was made of a polyoxyethylenepolyoxypropylene block copolymer having the structure generically shown above as Formula IV and having a polyoxypropylene hydrophobe base average molecular weight of about 4000, a total average molecular weight of about 111,500 and containing oxyethylene groups in the amount of about 70% by weight of the total weight of copolymer. This copolymer (Formula VI below) is sold under the trademark PLURONIC® F-127 (also known as Poloxamer 407) by the BASF Corporation, Parsippany, N.J. A solution in TRIS hydrochloride buffer was made by dissolving said polymer in cold (4° C.) buffer to give a concentration of 25% by weight in accordance with the cold process procedure described above for forming aqueous solutions. More specific solution procedures are described in "Artificial Skin I Preparation and Properties of PLURONIC® F-127 Gels for Treatment of Burns", *Journal of Biomedical Material Research* 6,527,1972, incorporated herein by reference. The block copolymer has the formula:

(VI)

This formulation forms the basis for the Figure in which curve A is the determined osmolality of the formulation in the liquid state and curve B is the calculated osmolality of the formulation in the gelled state. It is noted that, generally, the formulation will gel at mammalian body temperatures only at concentrations of polymer exceeding 17%.

The formulation was sterilized by autoclaving at 121° C. and 15 psi for 15 minutes. The pH before autoclaving was found to be 7.3 and after autoclaving remained the same. The osmolality in the gelled state before autoclaving was determined to be 290±10 mOsm/kg. The gel strength (viscosity) in centipoise as measured at 37° C. using a Brookfield (spindle and cup) viscometer at 20 revolutions per minute was greater than 44,000 before autoclaving and greater than 44,000 after autoclaving.

EXAMPLE 2

This is an example of an iso-osmotic, isotonic, pH balanced, thermoreversible system, in which the active ingredient is dissolved. The following antibiotic formulation was prepared to contain 3.5 mg. of neomycin sulfate and 10,000 units of polymyxin B sulfate per gram of antibiotic formulation solution. The antibiotic formulation was prepared as follows:

| Ingredient | Proportions by Weight |
|---|---|
| Neomycin sulfate | 0.55 |
| Polymyxin B sulfate | 0.12 |
| Glycerin | 0.7 |
| Poloxamer 407 (BASF) | 19.0 |
| Methyl/Propyl Parabens (9:1) | 0.1 |
| TRIS hydrochloride buffer (0.1 molar) | 79.53 |

The formulation was prepared by dissolving the methyl/propyl paraben preservative, neomycin sulfate and polymyxin B sulfate by stirring in the required amount of TRIS hydrochloride buffer. These ingredients in a glass beaker were placed on ice and the Poloxamer 407 was added to the beaker slowly while stirring. After the Poloxamer 407 was completely dissolved, the formulation was stored at 4° C. The product obtained was characterized as clear, colorless and exhibiting gelation at the temperature of mammalian skin (33°±2° C.). The formulation was sterilized by autoclaving for 15 minutes at 15 psi and 121° C. The pH and osmolality of the product were as follows: pH 7 and osmolality approximately 650 mOsm/kg in the liquid state. In the gelled state, the pH and osmolality of the preparation would be expected to be pH 7.5 and osmolality approximately 290 mOsm/kg, since the Poloxamer 407 molecules when gelled do not contribute to the osmotic force.

EXAMPLE 3

This is an example of an iso-osmotic, isotonic, pH balanced, thermoreversible system, in which the active ingredient is dispersed.

The following antibacterial formulation was prepared to contain one percent by weight of silver sulfadiazine.

| Ingredient | Proportions by Weight |
|---|---|
| Silver Sulfadiazine | 1.0 |
| Glycerin | 0.25 |
| Xanthan Gum | 0.33 |
| Poloxamer 407 (BASF) | 18.66 |
| Methyl/Propyl Parabens (9:1) | 0.1 |
| TRIS Maleate Buffer (0.05 molar) | 79.72 |

The formulation was prepared by levigating silver sulfadiazine and glycerin in a glass mortar. Weighed amounts of xanthan gum paste (2.5% in a buffer portion) were added with continued levigation. The poloxamer 407 and the methyl/propyl paraben preservatives were added to the other buffer portion, in accordance with the cold process described above, to prepare an aqueous solution. This solution was weighed and mixed with a weighed amount of levigated mix. The mixing was achieved with a homogenizer and in a nitrogen environment. The product obtained was characterized as milky-white and exhibiting gelation at the temperature of mammalian skin (33°±2° C.). The pH of the product was 7.32 and the measured osmolality in the liquid state was 573 mOsm/kg. The calculated osmolality in the gelled state was approximately 290 mOsm/kg.

EXAMPLES 4 AND 5

Examples 2 and 3 are repeated substituting 2% by weight of polymer #2, as described in U.S. Pat. No. 4,810,503 and 4% by weight of surfactant #1, as described therein. The balance of the percentage of Poloxamer 407 used in Examples 2 and 3 is made up with TRIS hydrochloride buffer. These formulations form gels at room temperature. Substantially similar pH and osmolality results are obtained.

While this invention has been described with reference to certain specific embodiments, it will be recognized by those skilled in the art that many variations are possible without departing from the scope and spirit of the invention, disclosed herein for the purpose of illustration, which do not constitute departures from the spirit and scope of the invention.

What is claimed is an exclusive property or privilege in the invention defined as follows:

1. A process for treating a condition requiring the use of a medical device or pharmacological treatment which comprises administering to the skin of a mammal a hypo-osmotic, iso-osmotic, or hyperosmotic composition comprising an aqueous gel, having a buffered pH and a desired osmolality, which is a liquid at room temperature or below and a gel at mammalian body temperature, said aqueous gel containing
   (1) about 80% to about 20% by weight of water and
   (2) about 10 to about 50% by weight of a polyoxyalkylene block copolymer of formula $$Y[(A)_n-E-H]_x \quad (I)$$

wherein A is a polyoxyalkylene moiety having an oxygen/carbon atom ratio of less than 0.5, x is at least 1, Y is derived from water or an organic compound containing x reactive hydrogen atoms, E is a polyoxyethylene moiety, n has a value such that the minimum molecular weight of A is between about 500 to about 900, as determined by the hydroxyl number of an intermediate of formula $$Y[(A)_n-H]_{x'} \quad (II)$$

and the total average molecular weight of the polyoxyalkylene block copolymer is between about 15000;
   wherein the osmolality of the composition in the liquid state is adjusted to achieve the desired value of the osmolality of the aqueous gel by assuming that the polyoxyalkylene block copolymer does not contribute to the osmolality in the aqueous gel.

2. The process of claim 1 wherein said composition is iso-osmotic to mammalian body tissues and further contains about 0.1 to about 60% by weight of a drug selected from the group consisting of antibacterials, antiinflammatories, antiparasitics, antivirals, local anesthetics, antifungals, analgesics, and diagnostics, wherein Y in said formulas I and II is a water soluble organic compound having 1-6 carbon atoms and said polyoxyalkylene block copolymer is selected from the group consisting of a polyoxyethylene-polyoxybutylene block copolymer, a polyoxyethylene-polyoxypropylene block copolymer and mixtures thereof, wherein the polyoxyethylene moiety constitutes at least 70% by weight of the polyoxyalkylene block copolymer, and where the pH is maintained at about 7.4±0.2, and the desired osmolality in the gel state is maintained at about 290 mOsm/kg.

3. The process of claim 2 wherein the polyoxyalkylene block copolymer is selected from polyoxyalkylene block copolymers which form aqueous gels at a concentration of about 10–50% by weight of the total weight of said composition.

4. The process of claim 3 wherein said Y is a compound selected from from the group consisting of propylene glycol, glycerin, pentaerythritol, trimethylolpropane, ethylenediamine, and mixtures thereof.

5. The process of claim 4 wherein Y is derived from propylene glycol, A is the residue of propylene oxide, and the intermediate of Formula II has an average molecular weight of at least about 900.

6. The process of claim 5 wherein Y is derived from butylene glycol, A is the residue of butylene oxide, and the intermediate of Formula II has an average molecular weight of at least about 500.

7. The process of claim 6 wherein said polyoxyalkylene block copolymer has the formula $$HO(C_2H_4O)_b(C_4H_8O)_a(C_2H_4O)_bH \quad (III)$$

wherein a and b are integers such that the hydrophobe base represented by $(C_4H_8O)_a$ has a molecular weight of at least 1000, as determined by hydroxyl number, the polyoxyethylene chain constitutes at least about 60% by weight of the polyoxyalkylene block copolymer, and the polyoxyalkylene block copolymer has a total average molecular weight of at least 15,000; or has the formula $$HO(C_2H_4O)_b(C_3H_6O)_a(C_2H_4O)_bH \quad (IV)$$

wherein a and b are integers such that the hydrophobe base represented by $(C_3H_6O)_a$ has a molecular weight of at least about 1500, as determined by hydroxyl number, the polyoxyethylene chain constitutes at least about 60% by weight of the polyoxyalkylene block copolymer, and the polyoxyalkylene block copolymer has a total average molecular weight of at least 15,000; or has the formula

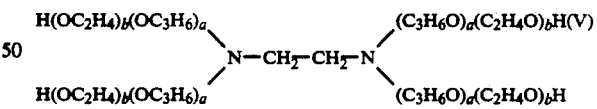

wherein a and b are integers such that the polyoxyalkylene block copolymer has a hydrophobe molecular weight of at least 2000, a hydrophile content of at least about 60% by weight, and a total average molecular weight of at least about 15,000.

8. The process of claim 7 wherein said copolymer is $$H[OCH_2CH_2]_{49}[OCHCH_2]_{67}[OCH_2CH_2]_{49}OH \overset{CH_3}{|} \quad (VI)$$

9. The process of claim 1 wherein said aqueous gel is hyperosmotic to mammalian body tissues.

10. The process of claim 1 wherein said aqueous gel is hypoosmotic to mammalian body tissues.

11. A process for treating a condition requiring the use of a medical device or administration of a pharmacological agent which comprises administering to the skin of a mammal a hypo-osmotic, iso-osmotic, or hyperosmotic composition comprising an aqueous gel with a buffered pH and a desired osmolality which composition is a gel at mammalian body temperature, said aqueous gel containing
 (1) present in an amount up to about 10% by weight of a combination of a surfactant and a polyoxyalkylene polyether having a molecular weight of about 10,000 to about 100,000, and
 (2) from about 80% to about 20% by weight of water;
wherein said polyether is selected from the group consisting of:
 (A) polyoxyalkylene polyethers prepared by reacting ethylene oxide and at least one lower alkylene oxide having 3 to 4 carbon atoms with at least one active hydrogen-containing compound having from 3 to 10 carbon atoms and from 3 to 6 active hydrogens to prepare a heteric or block copolymer intermediate and further reacting said copolymer intermediate with at least one alpha-olefin oxide having an average carbon chain length of about 20 to 45 aliphatic carbon atoms and wherein said alpha-olefin oxide is present in the amount of about 0.3 to 10 percent by weight based upon the total weight of said polyether, and
 (B) polyoxyalkylene polyethers prepared by reacting ethylene oxide with at least one active hydrogen-containing compound having from 2 to 10 carbon atoms and from 2 to 6 active hydrogens to prepare a homopolymer intermediate and further reacting said homopolymer intermediate with at least one alpha-olefin oxide having an average carbon chain length of about 20 to 45 aliphatic carbon atoms and wherein said alpha-olefin oxide is present in the amount of about 0.3 to 10 percent by weight based on the total weight of said polyether; wherein the osmolality of the composition is adjusted to achieve the desired value of the osmolality of the aqueous gel by assuming that the polyoxyalkylene polyether does not contribute to the osmolality in the aqueous gel.

12. The process of claim 11 wherein said composition is iso-osmotic to mammalian body tissues and further contains about 0.1 to about 60% by weight of a drug selected from the group consisting of antibacterials, anti-inflammatories, antiparasitics, antivirals, local anesthetics, antifungals, analgesics, and diagnostics and said polyether is prepared using a heteric copolymer intermediate and wherein the pH is maintained at about 7.4±0.2, and the desired osmolality in the gel state is maintained at about 290 mOsm/kg.

13. The process of claim 12 wherein said polyether is prepared using an alpha-olefin oxide having an average carbon length of about 20 to 30 carbon atoms, present in the amount of about 0.3 to 10 percent of the total weight of said polyether.

14. The process of claim 13 wherein said polyether contains a proportion of ethylene oxide residue to the residue of said lower alkylene oxide of about 70 to about 90 percent by weight of ethylene oxide residue to about 30 to about 10 percent by weight of said lower alkylene oxide residue.

15. The process of claim 14 wherein said polyether is prepared using propylene oxide as the lower alkylene oxide.

16. The process of claim 11 wherein said polyether is prepared using a block copolymer intermediate.

17. The process of claim 16 wherein said polyether is prepared using an alphaolefin oxide having an average carbon chain length of about 20 to 30 carbon atoms, present in the amount of about 0.3 to 10 percent of the total weight of said polyether.

18. The process of claim 17 wherein said polyether is prepared using a proportion of ethylene oxide residue of said lower alkylene oxide of from about 70 to about 90 percent by weight of ethylene oxide residue to about 30 to about 10 percent by weight of said lower alkylene oxide residue.

19. The process of claim 18 wherein said polyether is prepared using propylene oxide as the alkylene oxide.

20. The process of claim 11 wherein said polyether is polyether (B).

21. The process of claim 20 wherein said polyether is prepared using an alphaolefin oxide having an average carbon chain length of about 20 to 30 carbon atoms, present in the amount of about 0.3 to 10 percent of the total weight of said polyether.

22. The process of claim 11 wherein said aqueous gel is hyperosmotic to mammalian body tissues.

23. The process of claim 11 wherein said aqueous gel is hypo-osmotic to mammalian body tissues.

* * * * *